(12) United States Patent
Shimp et al.

(10) Patent No.: US 8,771,719 B2
(45) Date of Patent: *Jul. 8, 2014

(54) SYNTHESIS OF A BONE-POLYMER COMPOSITE MATERIAL

(75) Inventors: Lawrence A. Shimp, Morganville, NJ (US); John M. Winterbottom, Jackson, NJ (US); Todd M. Boyce, Aberdeen, NJ (US); David Knaack, Holmdel, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1505 days.

This patent is subject to a terminal disclaimer.

(21) Appl. No.: 10/639,912

(22) Filed: Aug. 12, 2003

(65) Prior Publication Data

US 2004/0146543 A1 Jul. 29, 2004

Related U.S. Application Data

(60) Provisional application No. 60/402,998, filed on Aug. 12, 2002.

(51) Int. Cl.
| | |
|---|---|
| *A61F 2/00* | (2006.01) |
| *A61K 35/32* | (2006.01) |
| *A01N 63/00* | (2006.01) |
| *A61L 27/46* | (2006.01) |
| *A61L 27/36* | (2006.01) |
| *A61L 27/48* | (2006.01) |

(52) U.S. Cl.
CPC .............. *A61L 27/48* (2013.01); *A61L 27/46* (2013.01); *A61L 27/3608* (2013.01)
USPC .......................... 424/423; 424/549; 424/93.7

(58) Field of Classification Search
None
See application file for complete search history.

(56) References Cited

U.S. PATENT DOCUMENTS

| | | | |
|---|---|---|---|
| 3,892,649 A | 7/1975 | Phillips et al. ............... 204/181 |
| 3,919,773 A | 11/1975 | Freeman ...................... 32/10 A |
| 4,547,327 A * | 10/1985 | Bruins et al. .................. 264/16 |
| 4,843,112 A * | 6/1989 | Gerhart et al. ............... 523/114 |
| 4,880,610 A | 11/1989 | Constantz |
| RE33,161 E | 2/1990 | Brown et al. |
| 4,902,508 A | 2/1990 | Badylak et al. |
| RE33,221 E | 5/1990 | Brown et al. |
| 5,034,059 A | 7/1991 | Constantz |
| 5,047,031 A | 9/1991 | Constantz |
| 5,053,212 A | 10/1991 | Constantz |
| 5,129,905 A | 7/1992 | Constantz |
| 5,149,368 A | 9/1992 | Liu et al. |
| 5,243,038 A | 9/1993 | Ferrari et al. |
| 5,262,166 A | 11/1993 | Liu et al. |
| 5,263,984 A | 11/1993 | Li et al. |
| 5,333,626 A | 8/1994 | Morse et al. ................. 128/898 |
| 5,336,264 A | 8/1994 | Constanz et al. |
| 5,462,722 A | 10/1995 | Liu et al. |
| 5,507,810 A | 4/1996 | Prewett et al. |
| 5,507,813 A * | 4/1996 | Dowd et al. ................ 623/23.63 |
| 5,513,662 A | 5/1996 | Morse et al. .................. 128/898 |
| 5,525,148 A | 6/1996 | Chow et al. |
| 5,542,973 A | 8/1996 | Chow et al. |
| 5,552,454 A | 9/1996 | Kretschmann et al. |
| 5,605,713 A | 2/1997 | Boltong et al. |
| 5,607,269 A | 3/1997 | Dowd et al. |
| 5,624,463 A | 4/1997 | Stone et al. |
| 5,650,176 A | 7/1997 | Lee et al. |
| 5,717,006 A | 2/1998 | Daculsi et al. |
| 5,837,752 A | 11/1998 | Shastri et al. |
| 5,846,484 A | 12/1998 | Scarborough et al. .......... 422/28 |
| 6,001,394 A | 12/1999 | Daculsi et al. |
| 6,002,065 A | 12/1999 | Constantz et al. |
| 6,027,744 A | 2/2000 | Vacanti et al. ................ 424/426 |
| 6,132,468 A | 10/2000 | Mansmann ................ 623/20.16 |
| 6,183,498 B1 | 2/2001 | Devore et al. |
| 6,206,957 B1 | 3/2001 | Driessens et al. |
| 6,294,187 B1 | 9/2001 | Boyce et al. |
| 6,352,667 B1 | 3/2002 | English .................... 264/328.17 |
| 6,376,573 B1 | 4/2002 | White et al. |
| 6,399,693 B1 * | 6/2002 | Brennan et al. ............... 524/494 |
| 6,432,436 B1 | 8/2002 | Gertzman et al. ............ 424/423 |
| 6,441,073 B1 | 8/2002 | Tanaka et al. |
| 6,616,698 B2 * | 9/2003 | Scarborough .............. 623/23.51 |
| 6,696,073 B2 | 2/2004 | Boyce et al. |
| 6,815,384 B2 * | 11/2004 | Ishikawa ........................... 501/1 |
| 6,933,328 B2 | 8/2005 | Schacht |
| 2002/0096222 A1* | 7/2002 | Ueno et al. .................... 137/828 |
| 2002/0098222 A1 | 7/2002 | Wironen et al. .............. 424/423 |
| 2003/0036800 A1* | 2/2003 | Meredith .................... 623/23.63 |
| 2003/0039676 A1 | 2/2003 | Boyce et al. |

(Continued)

FOREIGN PATENT DOCUMENTS

EP 470305 A1 * 2/1992

OTHER PUBLICATIONS

Deb et al., Hydroxyapatite-polyethylene composites: effect of grafting and surface treatment of hydroxyapatite, Journal of Materials Science: Materials in Medicine 7(1996)191-193.*

Nazhat, S.N., et al., "Dynamic Mechanical Behaviour of Modified Hydroxyapatite Reinforced Polyethylene Composites", *Fifth World Biomaterials Congress*, p. 83, May 29-Jun. 2, 1996.

Kimberly A. Hooper, et al., "Diphenolic Monomers Derived from the Natural Amino Acid α-L-Tyrosine: An Evaluation of Peptide Coupling Techniques", *Journal of Bioactive and Compatible Polymers* 10, 327-340 (1995).

(Continued)

*Primary Examiner* — Michael G Hartley
*Assistant Examiner* — Nabila Ebrahim
(74) *Attorney, Agent, or Firm* — Sorell Lenna & Schmidt LLP

(57) ABSTRACT

A method of producing a bone-polymer composite. The method comprises the steps of providing a plurality of bone particles, combining the bone particles with a polymer precursor, and polymerizing the polymer precursor.

26 Claims, 2 Drawing Sheets

(56) References Cited

U.S. PATENT DOCUMENTS

| | | |
|---|---|---|
| 2003/0045942 A1 | 3/2003 | Lai et al. |
| 2003/0114552 A1 | 6/2003 | Schacht |
| 2003/0144743 A1 | 7/2003 | Edwards et al. |
| 2003/0180344 A1 | 9/2003 | Wise et al. |
| 2003/0236573 A1 | 12/2003 | Evans et al. |
| 2004/0024457 A1 | 2/2004 | Boyce et al. |
| 2004/0034434 A1 | 2/2004 | Evans et al. |
| 2004/0064193 A1 | 4/2004 | Evans et al. |
| 2004/0138758 A1 | 7/2004 | Evans et al. |
| 2004/0146543 A1 | 7/2004 | Shimp et al. |
| 2005/0008620 A1 | 1/2005 | Shimp et al. |
| 2005/0008672 A1 | 1/2005 | Winterbottom et al. |
| 2005/0013793 A1 | 1/2005 | Beckman et al. |
| 2005/0031578 A1 | 2/2005 | Deslauriers et al. |
| 2005/0129726 A1 | 6/2005 | Liebschner |
| 2005/0238683 A1 | 10/2005 | Adhikari et al. |
| 2005/0281856 A1 | 12/2005 | McGlohorn et al. |

OTHER PUBLICATIONS

Satish Pulapura, et al., "Tyrosine-Derived Polycarbonates: Backbone-Modified "Pseudo"-Poly (Amino Acids) Designed for Biomedical Applications", *Biopolymers* 32, 411-417 (1992).

Simmons, D.M., et al., "Evaluation of collagen cross-linking techniques for the stabilization of tissue matrices", *Biotechnol. Appl. Biochem.* 17, 23-29 (1993) (abstract only).

Zhiyuan Zhong, et al., "Calcium methoxide initiated ring-opening polymerization of $\epsilon$-caprolactone and L-lactide", *Polymer Bulletin* 46, 51-57 (2001).

Varawut Tangpasuthadol, "Thermo-Mechanical Properties and Hydrolytic Degradation of Tyrosine-Derived Polymers for Use in Biomedical Applications", Ph.D. Dissertation, Rutgers, The State University of New Jersey, (Jan. 1999).

Baker, Gregory L., http://www.cem.msu.edu/~gradoff/brochf/Baker.htm, printed Aug. 2002.

"Silane Coupling Agent", http://www.apr.co.kr/silaneen.htm, printed Aug. 7, 2002.

Schmitz, et al., "A Preliminary Study of the Osteogenic Potential of a Biodegradable Alloplastic-Osteoinductive Alloimplant", *Clinical Orthopaedics and Related Research*, 237:245-255 (1988).

Bosch, P., "Bone Grafting With Fibrin Glue," *Wiener Klinische Wochenschrift Supplementum* 93(124): 3-26, 1981. (English Abstract Only).

International Search Report for PCT/US03/25417.

International Search Report for PCT/US03/39704.

Boesch, P., "Bone Grafting with Fibrin Glue", *Wiener Klinische Wochenschrift Supplementum*, 93, No. 124, pp. 3-26, 1981.

Han, et al., "Synergistic Effects of Lecithin and Human DBM on Bone Induction in Nude Rats", *Society for Biomaterials*, 28th Annual Meeting Transactions, 2002 (abstract).

Whittaker, et al., "Matrix Metalloproteinases and their Inhibitors—Current Status and Future Challenges", *Celltransmissions*, 17, prior to Jun. 13, 2002.

U.S. Appl. No. 10/681,651, filed Oct. 8, 2003, Shimp, et al.

U.S. Appl. No. 10/735,135, filed Dec. 12, 2003, Winterbottom, et al.

Goma et at, "Novel Biodegradable Polyurethanes for Medical Applications", *Synthetic Bioabsorbable Polymers for Implants, ASTM STP 1396*, Agrawal (et al.) eds., American Society for Testing and Materials, West Conshohocken, PA, 39-57, 2000.

Gunatillake of al., "Biodegradable Synthetic Polymers for Tissue Engineering", *European Cells and Materials*, 5: 1-16, 2003.

Lewandrowski et al., "Kinetics of cortical bone demineralization: Controlled demineralization—a new method for modifying cortical bone allografts", *J Biomed Materials Res.*, 31: 365-72, 1996.

Morlock et al., "Duration and frequency of every day activities in total hip patients", *J. Biomech.*, 34: 873-81, 2001.

Reddi et al., "Biochemical sequences in the transformation of normal fibroblasts in adolescent rats", *Proc. Nat. Acad. Sci. USA*, 69(6): 1601-5, 1972.

Urist, "A morphogenetic matrix for differentiation of bone tissue", *Calcif. Tissue Res.*, 4(Suppl): 98-101, 1970.

Urist, "Bone: formation by autoinduction", *Science*, 150(3698); 893-9, 1965.

Weiner, "Evolution of Biomineralization", *On Biomineralization*, Oxford University Press, 227-251, 1989.

Zhang at al., "A new peptide-based urethane polymer: synthesis, biodegradation, and potential to support cell growth in vitro", *Biomaterials*, 21: 1247-58, 2000.

Zhang et al., "Synthesis, Biodegradability, and Biocompatibility of Lysine Diisocyanate-Glucose Polymers", *Tis. Eng.*, 8(5): 771-85, 2002.

Zhang et al., Three-dimensional biocompatible ascorbic acid-containing scaffold for bone tissue.

\* cited by examiner

SYNTHESIS OF A BONE-POLYMER COMPOSITE MATERIAL

This application claims the priority of U.S. Provisional application No. 60/402,998, filed Aug. 12, 2002, the entire contents of which are incorporated herein by reference.

FIELD OF THE INVENTION

This invention pertains to the synthesis of composite materials for use in orthopedic applications, and, more specifically, to the synthesis of bone-reinforced polymer matrix composites.

BACKGROUND OF THE INVENTION

Vertebrate bone is a composite material composed of impure hydroxyapatite, collagen, and a variety of noncollagenous proteins, as well as embedded and adherent cells. Vertebrate bone can be processed into an implantable biomaterial, such as an allograft, for example, by removing the cells, leaving behind the extracellular matrix. The processed bone biomaterial can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone or may alternatively be processed into soft, moldable or flowable demineralized bone biomaterials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the bone is unable to support physiologic loading. Metal pins, screws, and meshes are frequently required to replace the mechanical functions of injured bone. However, metal is significantly stiffer than bone. Use of metal implants may result in decreased bone density around the implant site due to stress shielding. Furthermore, metal implants are permanent and unable to participate in physiological remodeling.

Bone's cellular healing processes, using bone tissue formation by ostoblast cells coordinated with bone and graft resorption by osteoclast cells, permit bone grafts and certain bone substitute materials to remodel into endogenous bone that is almost indistinguishable from the original. However, the use of bone grafts is limited by the available shape and size of grafts and the desire to optimize both the mechanical strength and the resorption rate. Bone substitute materials and bone chips are quickly remodeled but cannot immediately provide mechanical support. In contrast, cortical bone grafts can support physiological stresses but remodel slowly.

U.S. Pat. Nos. 6,294,187, 6,332,779, 6,294,041, 6,123, 731, 5,899,939, 6,478,825, 6,440,444, and 5,507,813, the contents of all of which are incorporated herein by reference, describes methods for preparing composites including allogenic bone for use in load bearing orthopedic applications. It is desirable to increase the strength of bone-reinforced composites by increasing the strength of the interactions with the matrix material.

SUMMARY OF THE INVENTION

In one aspect, the invention is a method of producing a bone-polymer composite. The method comprises the steps of providing a plurality of bone particles, combining the bone particles with a polymer precursor and polymerizing it. The bone particles may be demineralized, nondemineralized, or a mixture of both demineralized and nondemineralized bone particles. The bone particles may be obtained from one or more of cortical bone, cancellous bone, cortico-cancellous bone. In addition, the source of the bone may be autogenous, allogenic, xenogenic, or some combination of these. In one embodiment, the bone particles are about 1-25%, about 26-50%, about 51-75% or about 76%-99% by weight of the composite. Alternatively or in addition, about 60% of the particles may be elongate.

A surface of the bone particles may be modified. For example, a silane coupling agent may be attached to the bone particles. The silane coupling agent includes an active group that is incorporated into the polymerized monomer. The active group may be monofunctional or multifunctional. In an alternative embodiment, a biomolecule, a small molecule, a bioactive agent, a non-biologically active material, an inorganic material, a mineral, or any combination of the above may be attached to the bone particles either directly or through the silane coupling agent. In addition, the moiety added to the bone particles may be incorporated into the polymerized precursor or linked thereto by covalent or non-covalent interactions. In another embodiment, collagen fibers at the surface of the bone particles are exposed. The collagen fibers may be frayed or cross linked. The exposed collagen fibers may be derivatized with a biomolecule, a small molecule, a bioactive agent, a non-biologically active material, an inorganic material, a mineral, or some combination of these. The bone particles may also be washed in phosphoric acid. Alternatively, the bone particles may be coated with the polymer precursor before being combined with a larger quantity of polymer precursor. At least a portion of the vascular and interstitial structure of the bone particles may be infiltrated with the polymer precursor.

The polymer precursor may form a biodegradable or non-biodegradable polymer or copolymer or a copolymer of biodegradable and non-biodegradable polymers. The mixture of the precursor and the bone particles may be placed in a mold before polymerization or after polymerization has been started but before the precursor is completely polymerized. Alternatively, the mixture of the polymer precursor with the bone particles may be placed in an implant site before polymerization or after the polymer precursor has been partially polymerized. In one embodiment, vacuum or solvent infiltration, pressure, or heat are used to enhance the infiltration of the polymer precursor into the bone particles.

A surface of the composite may be modified after polymerization. For example, a portion of the surface may be oxidized, etched, or roughened. A biomolecule, small molecule, bioactive agent, or some combination of the above may be retained on the surface instead of or in addition to the oxidation or roughening. The composite may be machined into a predetermined shape following polymerization. A plurality of machined pieces may be fastened together, for example, with an adhesive, a mechanical fastener, ultrasonic bonding, or some combination of the above. In an alternative embodiment, the composite may be machined into particles and compressed to form an osteoimplant. The compressive force may be greater than 1,000 psi. For example, between about 2,500 and about 60,000 psi. In one embodiment, the compressed composite particles are a void volume not greater than 32% Before compressing, the composite particles may be combined with a biocompatible binder, filler, fiber, plasticizer, biostatic, biocidal agent, surface active agent, biomolecule, small molecule, bioactive agent, or any combination of the above. The composite particles may also be formed into an osteoimplant by wet-laying. In an alternative embodiment, at least a portion of the composite is heated to a temperature at which polymer flows. The at least partially melted composite may be placed in an implant site before cooling.

In another aspect, the invention is a composition comprising a plurality of bone particles, and a polymer precursor, for example, a monomer, prepolymer, flowable polymer, or partially-polymerized biocompatible polymer, wherein at least a portion of the bone particles are covalently attached to the polymer precursor or, after polymerizing, to the polymerized polymer precursor.

BRIEF DESCRIPTION OF THE DRAWING

The invention is described with reference to the several figures of the drawing, in which.

DEFINITIONS

Figure 1A:
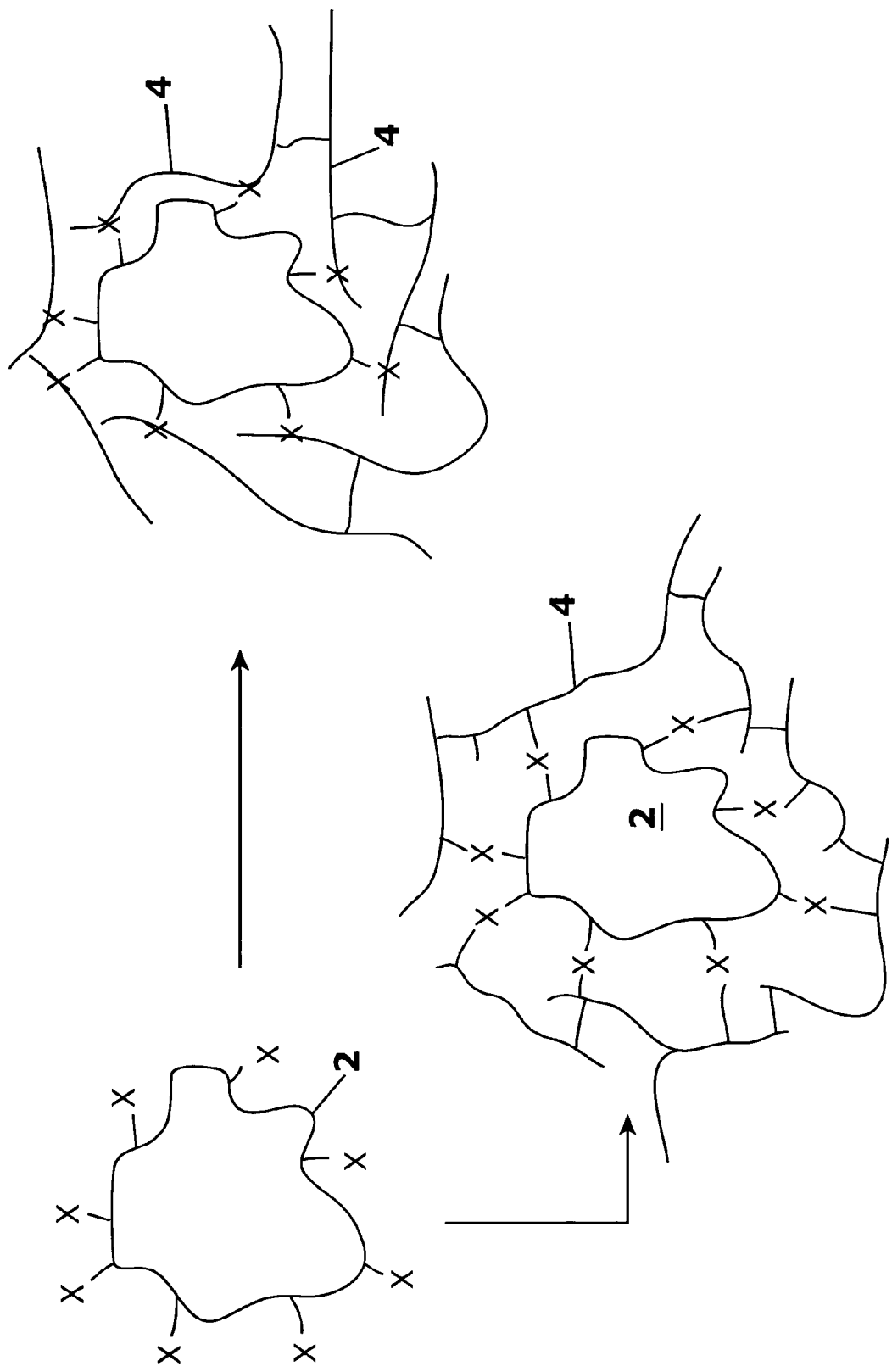
FIG. 1A is a schematic of two methods of incorporating a chemical moiety on a bone particle into a polymer according to an exemplary embodiment of the invention.

"Biomolecules": The term "biomolecules," as used herein, refers to classes of molecules (e.g., proteins, amino acids, peptides, polynucleotides, nucleotides, carbohydrates, sugars, lipids, nucleoproteins, glycoproteins, lipoproteins, steroids, etc.) that are commonly found in cells and tissues, whether the molecules themselves are naturally-occurring or artificially created (e.g., by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible," as used herein is intended to describe materials, upon administration in vivo, do not induce undesirable long term effects.

"Biodegradable": As used herein, "biodegradable" materials are materials that degrade under physiological conditions to form a product that can be metabolized or excreted without damage to organs. Biodegradable materials are not necessarily hydrolytically degradable and may require enzymatic action to fully degrade. Biodegradable materials also include materials that are broken down within cells.

"Mineral": As used herein, a "mineral" is a naturally occurring inorganic solid having a defined crystal structure and a chemical composition that may be exact or variable in its composition, or a naturally occurring solid element.

"Polynucleotide," "nucleic acid," or "oligonucleotide": The terms "polynucleotide," "nucleic acid," or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide," "peptide," or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polysaccharide", "carbohydrate" or "oligosaccharide": The terms "polysaccharide," "carbohydrate," or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis) that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present invention.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, including but not limited to protease and reverse transcriptase inhibitors, fusion inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, and imaging agents. In a certain preferred embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

DETAILED DESCRIPTION OF CERTAIN PREFERRED EMBODIMENTS

Figure 1B:
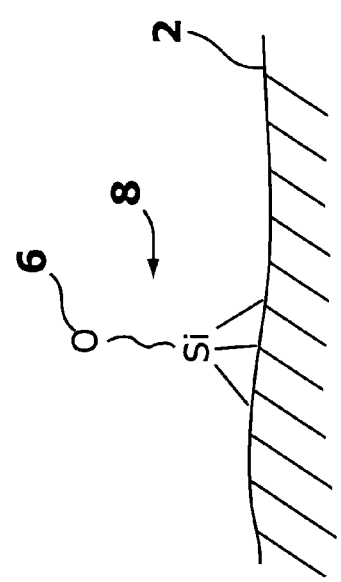
FIG. 1B is a schematic of a silane tether for use in an exemplary embodiment of the invention

The invention is a method of synthesizing a bone-polymer composite by integrating bone with the polymeric matrix at the time of synthesis or polymerization of the polymer. The bone is processed to form pieces of a predetermined size and combined with the monomer, which is then polymerized. The polymerized composite may be used immediately or may be further processed to form an osteoimplant. In one embodiment, a chemical group X on the surface of the bone particles (e.g., bone particle 2, FIG. 1A) is incorporated into the backbone of polymer 4 or bound to the polymer 4 during polymerization. For example, X may be an active group 6 at the end of silane 8 (FIG. 1B).

The composite of the invention may serve as a bone substitute material, provide a structural, weight bearing implant to replace a portion of or a whole bone, or provide a convenient source of bone derived particles for use in producing osteoimplants, for example, using the techniques of our commonly owned U.S. Pat. Nos. 6,294,187, 6,294,041, and 5,507,813 and other techniques that exploit bone particles. Bone particles are not always available in a shape that is convenient or useful either for machining into pieces of the correct size and shape for fashioning into an implant or for use in load-bearing applications. The techniques of the invention enable bone particles from any source and of any size and shape, to be used to produce osteoimplants. One skilled in the art will recognize that the size of the bone particles should be optimized according to several factors, including but not limited to the size and shape of the implant, the desired degradation rate, the mechanical strength, modulus, and other mechanical properties of the surrounding tissue, the expected load magnitude and direction, and the desired interactions with the surrounding tissue.

Preparation of Bone

The bone particles employed in the preparation of the bone particle-containing composition can be obtained from cortical, cancellous, and/or corticocancellous bone which may be of autogenous, allogenic and/or xenogeneic origin. Preferably, the bone particles are obtained from cortical bone of allogenic origin. Porcine and bovine bone are particularly advantageous types of xenogeneic bone tissue that can be used individually or in combination as sources for the bone particles. Particles are formed by milling whole bone to produce fibers, chipping whole bone, cutting whole bone, fracturing whole bone in liquid nitrogen, or otherwise disintegrating the bone tissue. Particles can optionally be sieved to produce particles of a specific size.

The bone particles employed in the composition can be powdered bone particles possessing a wide range of particle sizes ranging from relatively fine powders to coarse grains and even larger chips. In one embodiment, powdered bone particles can range in average particle size from about 0.05 to about 1.2 mm and possess an average median length to median thickness ratio of from about 1:1 to about 3:1. If desired, powdered bone particles can be graded into different sizes to reduce or eliminate any less desirable size(s) of particles which may be present. As particles of bone become smaller, they will contribute less to the mechanical strength of the implant and act more as filler. Still, the combination of bone powder and a polymer both reduces the amount of bone that is required to prepare the implant and eliminates shape constraints on the bone itself, since the polymer may be molded into a desired shape.

Alternatively, or in combination with the aforementioned bone powder, bone particles generally characterized as elongate and possessing relatively high median length to median thickness ratios can be utilized herein. Such elongate particles can be readily obtained by any one of several methods, e.g., by milling or shaving the surface of an entire bone or relatively large section of bone. Employing a milling technique, one can obtain a mass of elongate bone particles containing, for example, at least about 60 weight percent of elongate bone particles possessing a median length of from about 2 to about 200 mm or more, a median thickness of from about 0.05 to about 2 mm, and a median width of from about 1 mm to about 20 mm. Such elongate bone particles can possess a median length to median thickness ratio of at least about 50:1 up to about 500:1 or more and a median length to median width ratio of from about 10:1 and about 200:1. The milling process may be optimized to adjust the size of the bone particles and the size distribution. The mechanical strength, elastic modulus, and anisotropy of the implant can be tailored by adjusting the weight percent of the various shapes (elongate, particlulate, etc.) of bone particles utilized in the composite. Any weight percent between 1 and 100%, e.g, about 1-25%, about 26-50%, about 51-75%, or about 75-99%, may be used.

Another procedure for obtaining elongate bone particles, particularly useful for pieces of bone of up to about 100 mm in length, is the bone processing mill described in commonly assigned U.S. Pat. No. 5,607,269, the entire contents of which are incorporated herein by reference. Use of this bone mill results in the production of long, thin strips which quickly curl lengthwise to provide tubular-like bone particles. If desired, elongate bone particles can be graded into different sizes to reduce or eliminate any less desirable size(s) of particles which may be present. In overall appearance, elongate bone particles can be described as filaments, fibers, threads, slender or narrow strips, etc.

The bone particles are optionally demineralized in accordance with known and conventional procedures in order to reduce their inorganic mineral content. Demineralization methods remove the inorganic mineral component of bone by employing acid solutions. Such methods are well known in the art, see for example, Reddi, et al., *Proc. Nat. Acad. Sci.*, 1972, 69:1601-1605, the contents of which are incorporated herein by reference. The strength of the acid solution, the shape of the bone particles and the duration of the demineralization treatment will determine the extent of demineralization. Reference in this regard may be made to Lewandrowski, et al., *J. Biomed. Mater. Res.*, 1996, 31: 365-372, the contents of which are also incorporated herein by reference.

In a preferred demineralization procedure, the bone particles are subjected to a defatting/disinfecting step, followed by an acid demineralization step. A preferred defatting/disinfectant solution is an aqueous solution of ethanol. Ethanol is a good solvent for lipids, and water is a good hydrophilic carrier that enables the solution to penetrate more deeply into the bone particles. Ordinarily, at least about 10 to about 40 percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, the demineralized bone particles are rinsed with sterile water to remove residual amounts of acid and thereby raise the pH. The bone particles are preferably dried, for example, by lyophilization, before incorporated into the composite. The bone particles may be stored under aseptic conditions until they are used or sterilized using known methods shortly before combining them with the monomer.

As utilized herein, the phrase "superficially demineralized" as applied to the bone particles refers to bone particles possessing at least about 90 weight percent of their original inorganic mineral content. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, preferably less than about 1, weight percent of their original inorganic mineral content. The unmodified term "demineralized" as applied to the bone particles is intended to cover any one or combination of the foregoing types of demineralized bone particles.

Mixtures or combinations of one or more of the above types of bone particles can be employed. For example, one or more of the foregoing types of demineralized bone particles can be employed in combination with nondemineralized bone particles, i.e., bone particles that have not been subjected to a demineralization process. To increase fracture toughness the composite must be strong when it is in tension. The particles of the composite must be bound in the matrix so that the load can be transferred from bone to polymer etc. If they are not bound the loads are not transferred. Bonding increases the compressive and tensile strength because it provides a connection through which loads may be transferred.

The bone particles in the composite also play a biological role. Non-demineralized bone particles bring about new bone ingrowth by osteoconduction, in which an advancing bone front binds to the particle surface. Demineralized bone particles likewise play a biological role in bringing about new bone ingrowth by osteoinduction, in which bone cells are recruited from the host tissue to regenerate bone at the implant site. Both types of bone particles are gradually remodeled and replaced by new host bone as degradation of the polymer and remodeling of the implant bone particles progress over time.

Surface Modification of Bone Particles

The bone particles may be optionally treated to enhance their interaction with the polymer or to confer some property to the particle surface. While some bone particles will interact readily with the monomer and be covalently linked to the polymer matrix, the surface of the bone particles may need to be modified to facilitate incorporation into polymers that do not bond well to bone, such as polylactides. Surface modification provides a chemical substance that is strongly bonded to the surface of the bone, preferably covalently.

In one embodiment, silane coupling agents are employed to link a monomer or initiator molecule to the surface of the bone. The silane has at least two sections, a set of three leaving groups and an active group. The active group may be connected to the silicon atom in the silane by a elongated tether group. An exemplary silane coupling agent is 3-trimethoxysilylpropylmethacrylate, available from Union Carbide. The three methoxy groups are the leaving groups, and the methacrylate active group is connected to the silicon atom by a propyl tether group. In a preferred embodiment, the leaving group is an alkoxy group such as methoxy or ethoxy. Depending on the solvent used to link the coupling agent to the bone, hydrogen or alkyl groups such as methyl or ethyl may serve as the leaving group. The length of the tether determines the intimacy of the connection between the polymer matrix and the bone particle. By providing a spacer between the bone particle and the active group, the tether also reduces competition between chemical groups at the particle surface and the active group and makes the active group more accessible to the monomer during polymerization.

In one embodiment, the active group is an analog of the monomer of the polymer matrix. For example, amine active groups will be incorporated into polyamides, polyurethanes, polycarbonates, and other polymer classes based on monomers that react with amines, even if the polymer does not contain an amine. Hydroxy-terminated silanes will be incorporated into polyamino acids, polyesters, and other polymer classes that include hydroxylated monomers. Aromatic active groups or active groups with double bonds will be incorporated into vinyl polymers and other polymers that grow by radical polymerization. It is not necessary that the active group be monofunctional. Indeed, it may be preferable that active groups that are to be incorporated into polymers via step polymerization be difunctional. A silane having two amines, even if one is a secondary amine, will not terminate a polymer chain but can react with ends of two different polymer chains. Alternatively, the active group may be branched to provide two reactive groups in the primary position.

An exemplary list of silanes that may be used with the invention is listed in Table 1. Silanes are available from companies such as Union Carbide, AP Resources Co. (Seoul, South Korea), and BASF. Where the silane contains a potentially non-biocompatible moiety as the active group, it should be used to tether a biocompatible compound to the bone particle using a reaction in which the non-biocompatible moiety is the leaving group. It may be desirable to attach the biocompatible compound to the silane before attaching the silane to the bone particle, regardless of whether the silane is biocompatible or not. The derivatized silanes may be mixed with silanes that can be incorporated directly into the polymer and reacted with the bone particles, coating the bone particles with a mixture of "bioactive" silanes and "monomer" silanes. U.S. Pat. No. 6,399,693 discloses composites of silane modified polyaromatic polymers and bone. Silane-derivatized polymers may be instead of or in addition to first silanizing the bone particles.

TABLE 1

N-beta-(Aminoethyl)-gamma-aminopropylmethyldimethoxysilane
N-beta-(Aminoethyl)-gamma-aminopropyltrimethoxysilane
gamma-Aminopropylmethyldiethoxysilane
gamma-Aminopropyltriethoxysilane
gamma-Aminopropyltrimethoxysilane
Bis(3-triethoxysilylpropyl)tetrasulfide
gamma-Chloropropyltriethoxysilane
gamma-Chloropropyltrimethoxysilane
gamma-Glycidoxypropyltrimethoxysilane
gamma-Mercaptopropyltrimethoxysilane
gamma-Methacryloxypropyltrimethoxysilane
Methyltriacetoxysilane (MTAS)
Methyltrimethoxysilane (MTMS)
Methyl tris-(butanone oxime) Silane (MOS)
Methyl Oximino Silane (MOS)
Methyl tris-(methyl ethyl ketoximo) Silane (MOS)
Phenyl tris-(butanone oxime) Silane (POS)
Phenyl Oximino Silane (POS)
Phenyl tris-(methyl ethyl ketoximo) Silane (POS)
Tetraethoxysilane (TEOS)
Tetra (methyl ethyl ketoximo) Silane (TOS)
Tetramethoxysilane (TMOS)
Vinyltriethoxysilane
Vinyltrimethoxysilane
Vinyl tris-(butanone oxime) Silane (VOS)
Vinyl Oximino Silane (VOS)
Vinyl tris-(methyl ethyl ketoximo) Silane (VOS)

The active group of the silane may be incorporated directly into the polymer or may be used to attach a second chemical group to the bone particle. For example, if a particular monomer polymerizes through a functional group that is not commercially available as a silane, the monomer may be attached to the active group.

Non-silane linkers may also be employed to produce the composites of the invention. For example, isocyanates will form covalent bonds with hydroxyl groups on the surface of hydroxyapatite ceramics (de Wijn, et al., "Grafting PMMA on Hydroxyapatite Powder Particles using Isocyanatoethylmethacrylate," Fifth World Biomaterials Congress, May 29-Jun. 2, 1996, Toronto, Calif.). Isocyanate anchors, with tethers and active groups similar to those described with respect to silanes, may be used to attach monomer-analogs to the bone particles or to attach chemical groups that will link covalently or non-covalently with a polymer side group. Polyamines, organic compounds containing one or more primary, secondary, or tertiary amines, will also bind with both the bone particle surface and many monomers and polymer side groups. Polyamines and isocyanates may be obtained from Aldrich.

Alternatively, a biologically active compound such as a biomolecule, a small molecule, or a bioactive agent is attached to the bone particle through the silane. For example, mercaptosilanes will react with the sulfur atoms in proteins to attach them to the bone particle. Aminated, hydroxylated, and carboxylated silanes will react with a wide variety functional groups. Of course, the silane may be optimized for the compound being attached to the bone particle.

Biologically active molecules can modify non-mechanical properties of the composite as it is degraded. For example, immobilization of a drug on the bone particle allows it to be gradually released at an implant site as the composite is degraded. Anti-inflammatory compounds embedded within the composite will control the cellular response long after the initial response to implantation of the composite. For example, if a piece of the composite fractures several weeks after implantation, immobilized compounds will reduce the intensity of any inflammatory response, and the composite will continue to degrade through hydrolytic processes. Compounds may also be immobilized on the bone that are designed to elicit a particular metabolic response or to attract cells to the implant site.

Some biomolecules, small molecules, and bioactive agents may also be incorporated into the polymer matrix. For example, many amino acids have reactive side chains. The phenol group on tyrosine has been exploited to form polycarbonates, polyarylates, and polyiminocarbonates (see Pulapura, et al., "Tyrosine-derived polycarbonates: Backbone-modified "pseudo"-poly(amino acids) designed for biomedical applications," Biopolymers, 1992, 32: 411-417; and Hooper, et al., "Diphenolic monomers derived from the natural amino acid α-L-tyrosine: an evaluation of peptide coupling techniques," J. Bioactive and Compatible Polymers, 1995, 10:327-340, the entire contents of both of which are incorporated herein by reference). Amino acids such as lysine, arginine, hydroxylysine, proline, and hydroxyproline also have reactive groups and are essentially tri-functional. Amino acids such as valine, which has an isopropyl side chain, are still difunctional. Such amino acids may be attached to the silane and still leave one or two active groups available for incorporation into a polymer.

Non-biologically active materials may also be attached to the bone particles. For example, radioopaque, luminescent, or magnetically active particles may be attached to the bone particles using the techniques described above. If a material, for example, a metal atom or cluster, cannot be produced as a silane or other group that reacts with calcium phosphate ceramics, then a chelating agent may be immobilized on the bone particle surface and allowed to form a chelate with the atom or cluster. As the bone is resorbed, these non-biodegradable materials are still removed from the tissue site by natural metabolic processes, allowing the degradation of the polymer and the resorption of the bone particles to be tracked using standard medical diagnostic techniques.

In an alternative embodiment, the bone particle surface is chemically treated before being derivatized or combined with a monomer. For example, non-demineralized bone particles may be rinsed with phosphoric acid, e.g., for 1 to 15 minutes in a 5-50% solution by volume. Those skilled in the art will recognize that the relative volume of bone particles and phosphoric acid solution (or any other solution used to treat the bone particles), may be optimized depending on the desired level of surface treatment. Agitation will also increase the uniformity of the treatment both along individual particles and across an entire sample of particles. The phosphoric acid solution reacts with the mineral component of the bone to coat the particles with calcium phosphate, which may increase the affinity of the surface for inorganic coupling agents such as silanes and for the polymer component of the composite. As noted above, the surface may be partially demineralized to expose the collagen fibers at the particle surface.

The collagen fibers exposed by demineralization are typically relatively inert but have some exposed amino acid residues that can participate in reactions. The collagen may be rendered more reactive by fraying the triple helical structure of the collagen to increase the exposed surface area and the number of exposed amino acid residues. This not only increases the surface area available for chemical reactions but for mechanical interaction with the polymer as well. Rinsing the partially demineralized bone particles in an alkaline solution will fray the collagen fibrils. For example, bone particles may be suspended in water at a pH of about 10 for about 8 hours, after which the solution is neutralized. One skilled in the art will recognize that this time period may be increased or decreased to adjust the extent of fraying. Agitation, for example, in an ultrasonic bath, may reduce the processing time. Alternatively, the particles may be sonicated with water, surfactant, alcohol, or some combination of these.

Alternatively, the collagen fibers may be cross-linked. A variety of cross-linking techniques suitable for medical applications are well known in the art. For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, "Evaluation of collagen cross-linking techniques for the stabilization of tissue matrices," *Biotechnol. Appl. Biochem.*, 1993, 17:23-29; PCT Publication WO98/19718, the contents of both of which are incorporated herein by reference). Alternatively, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link the collagen. The bone particles are then washed to remove all leachable traces of the material. Enzymatic cross-linking agents may also be used. One skilled in the art will easily be able to determine the optimal concentrations of cross-linking agents and incubation times for the desired degree of cross-linking.

Both frayed and unfrayed collagen fibers may be derivatized with monomer, prepolymer, initiator, and/or biologically active or inactive compounds, including but not limited to biomolecules, bioactive agents, small molecules, inorganic materials, minerals, through reactive amino acids on the collagen fiber such as lysine, arginine, hydroxylysine, proline, and hydroxyproline. Monomers that link via step polymerization may react with these amino acids via the same reactions through which they polymerize. Vinyl monomers and other monomers that polymerize by chain polymerization may react with these amino acids at the double bond. Vinyl monomers and other monomers that polymerize by chain polymerization may react with these amino acids via their reactive pendant groups, leaving the vinyl group free to polymerize.

Additionally or alternatively, the surface treatments described above or treatments such as etching may be used to increase the surface area or surface roughness of the bone particles. Such treatments increase the interfacial strength of the bone/polymer interface by increasing the surface area of the interface and/or the mechanical interlocking of the bone particles and the polymer.

Preferably, surface treatments of the bone particles are optimized to enhance covalent attractions between the bone particles and the polymer matrix of the composite. In an alternative embodiment, the surface treatment may be designed to enhance non-covalent interactions between the bone particle and the polymer matrix. Exemplary non-covalent interactions include electrostatic interactions, hydrogen bonding, pi-bond interactions, Van der Waals interactions, and mechanical interlocking. For example, if a protein or a polysaccharide is immobilized on the bone particle, the chains of the polymer matrix will become physically entangled with the long chains of the biological polymer as they polymerize. Charged phosphate sites on the surface of the bone, produced by washing the bone particles in basic solution, will interact with the carbonyl and carboxylate groups present in many biocompatible polymers, especially those based on amino acids. The pi-orbitals on aromatic groups immobilized on a bone particle will interact with double bonds and aromatic groups in the polymer matrix.

Combining the Bone Particles with a Polymer Precursor

To form the composite, the bone particles are combined with a polymer precursor. Exemplary polymer precursors include monomer, partially polymerized polymer, flowable polymer, or prepolymer. A polymer may be flowable because it was heated past its melting point or because it has an extremely low molecular weight. Such precursors are polymerized by further crosslinking or polymerization after combination with bone particles to form a composite in which the polymer is covalently linked to the bone particles. A prepolymer is a low molecular weight oligomer typically produced through step growth polymerization. The prepolymer is formed with an excess of one of the difunctional components to produce molecules that are all terminated with the same group. For example, a diol and an excess of an diisocyanate may be polymerized to produce isocyanate terminated prepolymer that may be combined with a diol to form a polyurethane.

The combination of the bone particles with a monomer involves both microstructural and macrostructural considerations. The microstructural considerations concern the degree of infiltration of the polymer within the bone. The macrostructural considerations concern the arrangement of the bone particles within the polymer.

Microstructural Considerations

In histology, thorough infiltration facilitates sectioning of tissue into thin slices for microscopic observation. However, the bone particles used in the invention may be incorporated into the polymer with a strong interfacial interaction, not necessarily infiltration of the polymer into the interstices between mineralized collagen fibers. Most of the monomers and other polymer precursors suggested for use with the invention are sufficiently flowable to penetrate through the channels and pores of trabecular bone surrounding the bone elements, even if they do not penetrate into the trabeculae (or into the mineralized fibrils of cortical bone). In an exemplary embodiment, the polymer precursor is able to infiltrate part of the vascular and/or interstitial structure of the bone particles. The vascular structure of bone includes such structures such as osteocyte lacunae, Haversian canals, Volkmann's canals, canaliculi and similar structures. The interstitial structure of the bone particles includes the spaces between trabeculae and similar features. Thus, it may only be necessary to incubate the bone particles in neat monomer or other polymer precursor for a period of time before initiating polymerization.

Vacuum infiltration may be used to help the polymer precursor infiltrate the lacunae and canals, and, if desired, the canaliculi. Indeed, if the polymer matrix of the composite completely infiltrates the mineralized fibrils of, for example, cortical bone, the mechanical properties of the bone particles may not contrast as greatly with the properties of the surrounding matrix because the matrix will be part of the bone. Penetration of the microstructural channels of the bone particles will maximize the surface area of the interface between the particles and the polymer matrix and prevent solvents and air bubbles from being trapped in the composite, e.g., between trabeculae. Vacuum infiltration, where appropriate, will also help remove air bubbles from the composite.

In another embodiment, infiltration may be achieved using solvent infiltration. Vacuum infiltration may be inappropriate for highly volatile monomers. Solvents employed for infiltration should carefully selected, as many of the most common solvents used for infiltration are toxic. Highly volatile solvents such as acetone will evaporate during infiltration, reducing the risk that they will be incorporated into the polymer and implanted into the body. Exemplary solvents for use with the invention include but are not limited to dimethylsulfoxide (DMSO) and ethanol. As is well known to those skilled in the art, solvent infiltration is achieved by mixing the bone particles with solutions of the solvent with the polymer precursor, starting with very dilute solutions and proceeding to more concentrated solutions and finally to neat precursor.

One skilled in the art will recognize that other standard histological techniques, including pressure and heat, may be used to increase the infiltration of the polymer precursor into the bone particles. Infiltrated bone particles may then be combined with a volume of fresh polymer precursor for polymerization and formation of the composite. Automated apparatus for vacuum and pressure infiltration include the Tissue Tek VIP Vacuum infiltration processor E150/E300, available from Sakura Finetek, Inc.

The interaction of the polymer with the bone particles may also be enhanced by coating individual bone particles with the polymer precursor before combining them with bulk precursor. The coating enhances the association of the polymer component of the composite with the bone particles. For example, individual bone particles may be spray coated with a monomer or prepolymer. Alternatively, the individual bone particles may be coated using a tumbler—bone particles and solid polymer precursor are tumbled together to coat the particles. A fluidized bed coater may also be used to coat the particles. In addition, the particles may simply be dipped into liquid or powdered polymer precursor. All of these techniques will be familiar to those skilled in the art.

Macrostructural Considerations

Whether or not the bone particles are first infiltrated with the monomer, the bone particles may be mixed with the monomer according to standard composite processing techniques. For example, regularly shaped particles may simply be suspended in the monomer. The monomer may be mechanically stirred to distribute the particles or bubbled with a gas, preferably one that is oxygen- and moisture-free.

Elongated bone particles may be aligned in the polymer matrix or randomly oriented. To align the particles, the particle-monomer mixture may be rolled, extruded, twisted, or otherwise mechanically aligned. Alternatively, the elongated particles may be deposited into the monomer as they are produced. For example, grated or milled bone particles tend to exit the apparatus roughly aligned with one another. Instead of being collected, the particles may be delivered directly from the mill to the monomer, onto which they will fall in roughly the same orientation, much like cheese passing through a plane grater. Producing randomly oriented particles is more difficult. Mechanical stirring usually produces area of local alignment. Bubbling may impart a slight upwards orientation but otherwise can effectively randomize the orientation of the particles. Agitation may also be effective to randomize orientation.

For non-demineralized bone, both elongated particles and regularly shaped particles will increase the stiffness and fracture toughness of the polymer matrix. For regularly shaped particles, the mechanical response will generally be isotropic. For elongated particles, the effect of the particles on the mechanical properties of the composite depend on the orientation of the particles within the polymer matrix. If the particles are oriented randomly, then their effect on the mechanical properties of the polymer matrix do not depend on the loading mode. If the particles are aligned, or nearly so, then their contribution to the mechanical properties of the composite depend on both the loading mode and the direction of load.

In a preferred embodiment, the bone particles in the composite, rather than reinforcing the polymer matrix, carry the load, while the polymer matrix holds the particles in place. For example, larger pieces of bone may be stacked on top of one another in a preform and monomer allowed to flow around the bone pieces, following which the monomer is polymerized. This allows structural implants of a desired shape to be produced from irregularly shaped pieces of bone. Bone has very high compressive strength; however, as for bricks, the forces exerted at the polymer-filled boundaries between bone pieces will have a shear component as well as a tensile or compressive component. As a result, the compressive strength of the composite will not only be determined by the compressive strength of the bone but by the shear strength of the composite. This shear strength is increased by the covalent attachment of the polymer to the bone particles, which will limit the movement of the polymer chains. In an alternative embodiment, the surfaces of the bone particles are demineralized and the exposed collagen of adjacent bone particles chemically linked using the techniques of our commonly owned U.S. Pat. No. 6,123,731, entitled Osteoimplant and Method for its Manufacture, the entire contents of which are incorporated herein by reference.

In a preferred embodiment, the composite is about 25-30% polymer by weight. Depending on the implant site, the shape of the bone particles, and the mechanical and degradation properties of the matrix, it may be desirable to use a higher or lower weight fraction of polymer in the composite. One skilled in the art will recognize that the volume fraction of the polymer will depend on the density of the polymer.

Polymerization of the Matrix

After the bone particles are combined with the polymer precursor, the matrix is polymerized. For example, a flowable polymer may be further polymerized or cross-linked. During polymerization, the polymer preferably is attached covalently to the bone particles. If the polymerizing precursor does not bind to calcium phosphate compounds, then the bone particles may be surface treated before being combined with the monomer, as described above.

Any biocompatible polymer may be used to form composites according to the invention. A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, *Acc. Chem. Res.* 33:94, 2000; Langer, *J. Control Release* 62:7, 1999; and Uhrich et al., *Chem. Rev.* 99:3181, 1999; all of which are incorporated herein by reference).

Preferably, the polymer matrix is biodegradable. Exemplary biodegradable materials include poly(arylates), poly(anhydrides), poly(hydroxy acids), polyesters, poly(ortho esters), poly(alkylene oxides), polycarbonates, poly(propylene fumerates), poly(caprolactones), polyamides, polyamino acids, polyacetals, polylactides, polyglycolides, poly(dioxanones), polyhydroxybutyrate, polyhydroxyvalyrate, poly(vinyl pyrrolidone), biodegradable polycyanoacrylates, biodegradable polyurethanes and polysaccharides. In one embodiment, the degradation products include bioactive materials, biomolecules, small molecules, or other such materials that participate in metabolic processes. Monomers for tyrosine-based polymers, including but not limited to polyarylates and polycarbonates may be prepared by reacting an L-tyrosine-derived diphenol compound with phosgene or a diacid (Hooper, 1995; Pulapura, 1992). Similar techniques may be used to prepare amino acid-based monomers of other amino acids having reactive side chains, including imines, amines, thiols, etc. Non-biodegradable polymers may also be used as well. For example, polypyrrole, polyanilines, polythiophene, and derivatives thereof are useful electroactive polymers that can transmit voltage from the endogenous bone to an implant. Other non-biodegradable, yet biocompatible polymers include polystyrene, non-biodegradable polyurethanes, polyureas, poly(ethylene vinyl acetate), polypropylene, polymethacrylate, polyethylene, and poly(ethylene oxide). Monomers that are used to produce any of these polymers are easily purchased from companies such as Polysciences, Sigma, and Scientific Polymer Products. Those skilled in the art will recognize that this is an exemplary, not a comprehensive, list of polymers appropriate for in vivo applications. Co-polymers, mixtures, and adducts of the above polymers may also be used with the invention.

The polymers of the composite may form by step or chain polymerization. One skilled in the art will recognize that the rate of polymerization should be controlled so that any change in volume upon polymerization does not impact mechanical stresses on the included bone particles. The amount and kind of radical initiator, e.g., photo-active initiator (e.g., UV or infrared), thermally-active initiator, or chemical initiator, or the amount of heat or light employed, may be used to control the rate of reaction or modify the molecular weight. Where desired, a catalyst may be used to increase the rate of reaction or modify the molecular weight. For example, a strong acid may be used as a catalyst for step polymerization. Trifunctional and other multifunctional monomers or cross-linking agents may also be used to increase the cross-link density. For chain polymerizations, the concentration of a chemical initiator in the monomer-bone particle mixture may be adjusted to manipulate the final molecular weight.

Exemplary initiators are listed in George Odian's *Principles of Polymerization*, (3rd Edition, 1991, New York, John Wiley and Sons) and available from companies such as Polysciences and Sigma. Alternatively, polymerized or partially polymerized material may be exposed to UV light, microwaves, or an electron beam to provide energy for inter-chain reactions. One skilled in the art will recognize how to modify the cross-link density to control the rate of degradation and the stiffness of the composite. Exemplary methods for controlling the rate of polymerization and the molecular weight of the product are also described in Odian (1991), the entire contents of which are incorporated herein by reference.

The composite may be polymerized in any shape. Exemplary shapes include, without limitation, a sheet, plate, particle, sphere, strand, coiled strand, capillary network, film, fiber, mesh, disk, cone, rod, cup, pin, screw, tube, tooth, tooth root, bone or portion of bone, wedge or portion of wedge, cylinder, and threaded cylinder. In one embodiment, the composite is polymerized in a mold having the shape of a desired implant. For example, a mold may be shaped as a portion of a bone or as a whole bone that is being replaced. The shape may encompass a diaphysial implant, an intercalary, or an intramedullary implant. Exemplary bones that may be replaced using the techniques of the invention include ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones.

In one embodiment, the composite is molded as a plate or similar support, including but not limited to an I-shape to be placed between teeth for intra-bony defects, a crescent apron for single site use, a rectangular bib for defects including both the buccal and lingual alveolar ridges, neutralization plates, spoon plates, condylar plates, clover leaf plates, compression plates, bridge plates, wave plates, etc. Partial tubular as well as flat plates may be fabricated using the composite of the invention. The composite may also be machined to form part or all of a hip implant, including the stem, head, and/or acetabular cup. When used for the cup, the machined implant may be lined with a desired articulation material, e.g., plastic or metal. Other joint replacement devices may also benefit from the techniques of the invention.

Alternatively, the composite may be a block that is machined into a desired shape after polymerization, as described below.

In an alternative embodiment, the monomer is charged into the implant site and polymerized in situ. Alternatively, the monomer may be partially polymerized into a prepolymer after mixing and then poured or injected into a mold or implant site where polymerization is completed. The monomer may be polymerized until the prepolymer is a semisolid putty. The prepolymer may be inserted into a wound site like standard bone substitute materials. After polymerization is complete, the wound site is "set" and no further covering or wrapping is required to retain the composite in the implant site.

Post-Polymerization Treatment of the Composite

After polymerization, the composite may be removed from the mold and either used immediately or manipulated chemically or mechanically. For example, the surface of the implant may be oxidized using a solvent or gas to break some of the polymer chains and accelerate the initial decomposition of the implant. The surface of the implant may be roughened using standard techniques to promote bony on-growth. For example, the surface of the implant may be sanded, filed, plasma etched, chemically etched, or mechanically pitted, for example, by sand blasting.

For example, composites having the shape of the desired implant may be further surface-treated to promote a desired cellular response. Techniques for attaching growth factors and other biomolecules to biocompatible polymers are well known to those skilled in the art. For example, the of the composite may be plasma etched to render the surface more reactive. A biomolecule, small molecule, or bioactive agent may be attached directly to the reactive surface or to a silane coupling agent attached to the etched surface (see U.S. Pat. Nos. 6,033,582 and 6,119,028, the entire contents of which are incorporated herein by reference). For example, anti-inflammatory agents or antibiotics may be attached to the surface of the implant to reduce inflammation and the risk of infection. Alternatively, growth factors may be attached to attract osteoblasts to the implant site or to stimulate the production of collagen.

Alternatively, the composite may be immersed in a solution of the desired compound, which is allowed to adsorb onto the surface by ion exchange, diffusion, or other mechanisms known to those skilled in the art. The surface of the composite may be treated, for example, by plasma etching or oxidation, to increase its affinity for the compound or increase surface area. The compound is retained on the composite by electrostatic interactions. While the compound may desorb shortly after implantation, it was chosen to influence the initial physiological response to the implant. Thus, rapid desorption in a physiological environment is desirable.

The implant may also be machined according to techniques well known to those skilled in plastic machining. For example, holes may be drilled into the implant to facilitate bony ingrowth or to provide channels for suturing tissues to the implant. Alternatively, a composite shaped as a block may be machined into a desired shape, including any of the shapes listed above. Computer-controlled lathes and other equipment enable a block to be shaped into complex three-dimensional shapes including curves, dimples, and other contours. Such a shape may be customized to fit a particular implant site. These machined components may be attached to one another using mechanical fasteners such as dowels, pins, and screws, all of which may be fabricated from the composite of the invention. Traditional joints such as tongue-and-groove, dovetail, or mortise-and-tenon may be employed as the machined pieces are assembled.

Alternatively or in addition, the machined pieces may be chemically attached to one another. For example, a biocompatible adhesive may be used to attach machined pieces to one another. Exemplary biocompatible adhesives include biocompatible cyanoacrylates, epoxy-based compounds, dental resin sealants, dental resin cements, glass ionomer cements, poly(methyl methacrylate) (e.g., bone cement), gelatin-resorcinol-formaldehyde glues, collagen-based glues, inorganic bonding agents such as zinc phosphate, magnesium phosphate, and other phosphate based cements, zinc carboxylate, and protein-based binders, including but not limited to fibrin glues and mussel-derived adhesive proteins. Ultrasonic bonding may also be exploited to attach machined pieces of the composite to one another.

Chemical linkage may also be achieved by causing the machined pieces to cross-link with one another. If there are bone particles at the surface of the composite, they may be linked to one other using standard cross-linking techniques, optionally after demineralization. Alternatively, the machined pieces may be plasma-etched or oxidized and then the opposing surfaces caused to form cross-links between the two pieces of composite.

If the arrangement of the bone particles within the composite is anisotropic, slices of the composite may be assembled in layers in which the direction of orientation of the bone particles is offset between layers. The layers may be offset by 30°, 60°, 90° or by some other angle, so that the bone particles appear to form a spiral through the stacked layers. The layers may be in a continuous ply or rotated ply configuration in which successive layers are continuously offset by some specified or random angle from the preceding layer.

In another embodiment, a block of the composite material may be milled or ground according to the techniques outlined in the section entitled "Preparation of Bone," above. The shaved, ground, or milled composite particles may be combined in a mold having a desired shape or configuration, including any of the shapes described above, and pressed to form a solid according to the teachings of U.S. Pat. No. 6,294,187, the entire contents of which are incorporated herein by reference. In a preferred embodiment, the composite particles incorporated into the pressed shape have the size and shape described in the '187 patent. The composite particles may be mixed with additional biocompatible components, including biocompatible binders, fillers, fibers, platicizers, biostatic/biocidal agents, surface active agents (e.g., surfactants), biomolecules, small molecules, bioactive agents, etc., prior to, during, or after compressing the composite particles.

Particles of the composite may also be reassembled to form an implant by wet-laying according to the techniques of U.S. Pat. No. 5,507,813, the entire contents of which are incorporated herein by reference. The composite particles are slurried in a suitable liquid and cast on a form such as a flat sheet, mesh screen, or a three-dimensional mold. The liquid may include additional biocompatible components as described above. The wet-laying process results in particle entanglement that helps the final implant retain its shape. Further adhesion between the composite particles may be achieved by including an adhesive in the liquid or by using ultrasonic bonding. The wet-laid mass is then dried by removing the liquid from the entangled mass by vacuum or evaporation. Alternatively or in addition, the entangled mass of composite particles may be subjected to a compressive force during or after wet-laying and/or while the mass of particles is being dried.

In an alternative embodiment, the completed composite is remelted and molded into a desired shape. Thermoplastic polymers will flow upon heating and may be reshaped without machining. The polymer may be rolled or extruded to form a particular shape or molded in the shape of a desired implant, as discussed above. In an alternative embodiment, the composite is at least partially melted and inserted into an implant site before cooling. Alternatively, a machined polymer may be heated briefly to reduce surface stresses caused by shear during machining.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A composition, comprising:
a plurality of bone particles having a surface modified with a silane coupling agent; wherein the bone particles are about 51% to about 75% by weight of the composition, or the bone particles are about 76% to about 99% by weight of the composition; and a polymer precursor selected from a monomer, and a prepolymer, wherein: when the polymer precursor is polymerized, at least a portion of the bone particles are covalently attached to the polymerized polymer precursor, at least a portion of the interstitial and vascular structure of the bone particles is infiltrated by the polymerized polymer precursor, or both and the composition comprises a polymer matrix having at least about 60% of the bone particles being elongated and randomly orientated in the polymer matrix and the polymer matrix comprises a biodegradable polyurethane.

2. The composition of claim 1 wherein at least a portion of the bone particles are covalently linked to the polymer precursor.

3. The composition of claim 1, wherein at least a portion of the interstitial and vascular structure of the bone particles are infiltrated with the polymer precursor.

4. The composition of claim 1, wherein the bone particles are selected from the group consisting of nondemineralized bone particles, demineralized bone particles, and mixtures thereof.

5. The composition of claim 1 wherein the bone particles are obtained from a member of the group consisting of cortical bone, cancellous bone, cortico-cancellous bone, and mixtures thereof.

6. The composition of claim 1, wherein the bone particles are obtained from a member of the group consisting of autogenous bone, allogenic bone, xenogeneic bone, and mixtures thereof.

7. The composition of claim 1 wherein the bone particles are about 51% to about 75% by weight of the composition.

8. The composition of claim 1, wherein the bone particles are about 76% to about 99% by weight of the composition.

9. The composition of claim 1, wherein the silane coupling agent comprises an active group that is incorporated into the polymerized polymer precursor.

10. The composition of claim 9, wherein the active group is monofunctional or multifunctional.

11. The composition of claim 1, wherein the surfaces of the bone particles are further modified with a moiety selected from the group consisting of a biomolecule, a small molecule, a bioactive agent, a non-biologically active material, an inorganic material, a mineral, and any combination of the above to the bone particles.

12. The composition of claim 1, wherein the silane coupling agent is derivatized modified with a moiety selected from the group consisting of a biomolecule, a small molecule, a bioactive agent, a non-biologically active material, an inorganic material, a mineral, and any combination of the above.

13. The composition of claim 11, wherein the moiety is incorporated into the polymerized polymer precursor and linked to the polymerized polymer precursor by a member of covalent interactions, non-covalent interactions, and any combination of the above.

14. The composition of claim 1 wherein the bone particles include exposed collagen fibers at the surface.

15. The composition of claim 14, wherein the exposed collagen fibers are frayed.

16. The composition of claim 14, wherein the exposed collagen fibers are cross-linked.

17. The composition of claim 14, wherein the exposed collagen fibers are derivatized with a moiety selected from the group consisting of a biomolecule, a small molecule, a bioactive agent, a non-biologically active material, an inorganic molecule, a mineral, and any combination of the above.

18. The composition of claim 1 wherein the bone particles comprise a coating of calcium phosphate.

19. The composition of claim 1, wherein the polymerized polymer precursor is a polymer comprising one or more of biodegradable, nonbiodegradable, co-polymers of biodegradable polymers, co-polymers of nonbiodegradable polymers, and co-polymers of biodegradable and non-biodegradable polymers.

20. The composition of claim 19, wherein the polymer further comprises one or more of poly(phosphoesters), polysulfones, polyfumarates, polyphosphazines, poly(alkylene oxides), poly(arylates), poly(anhydrides), poly(hydroxy acids), polyesters, poly(ortho esters), polycarbonates, poly(propylene fumerates), poly(caprolactones), polyamides, polyamino acids, polyacetals, polylactides, polyglycolides, poly(dioxanones), polyhydroxybutyrate, polyhydroxyvalyrate, poly(vinyl pyrrolidone), biodegradable polycyanoacrylates, polysaccharides, tyrosine-based polymers, poly(pyrrole), poly(aniline), poly(thiophene), polystyrene, nonbiodegradable polyurethanes, polyureas, poly(ethylene vinyl acetate), polypropylene, polymethacrylate, polyethylene, poly(ethylene oxide), and mixtures, adducts, and copolymers thereof.

21. The composition of claim 1, wherein the plurality of bone particles are compressed together in a predetermined shape.

22. The composition of claim 21, wherein the compressed particles have a void volume not greater than 32%.

23. The composition of claim 21, further comprising a member of a biocompatible binder, filler, fiber, plasticizer, biostatic/biocidal agent, surface active agent, biomolecule, small molecule, bioactive agent, and any combination of the above.

24. The composition of claim 21, wherein the shape is selected from a shape selected from the group consisting of a bone, a section of a bone, sheet, particle, sphere, strand, coiled strand, capillary network, film, fiber, mesh, plate, disk, cone, pin, screw, tube, cup, tooth, tooth root, strut, wedge, portion of wedge, cylinder, threaded cylinder, and rod.

25. The composition of claim 12, wherein the moiety is incorporated in the polymerized polymer precursor and linked to the polymerized polymer precursor by a member of covalent interactions, non-covalent interactions, and any combinations of the above.

26. The composite of claim 1, wherein the silane coupling agent comprises one or more of N-beta-(Aminoethyl)-gamma-aminopropylmethyldiethoxysilane, N-beta-(Aminoethyl)-gamma-aminopropyltrimethoxysilane, gamma-Aminopropylmethyldiethoxysilane, gamma-Aminopropyltriethoxysilane, gamma-Aminopropyltrimethoxysilane, Bis(3-triethoxysilylpropyl) tetrasulfide, gamma-Chloropropyltriethoxysilane, gamma-Chloropropyltrimethoxysilane, gamma-Glycidopropyltrimethoxysilane, gamma-Mercaptopropyltrimethoxysilane, gamma-Methacryloxypropyltrimethoxysilane, Methyltriacetoxysilane, Methyltrimethoxysilane, Methyl tris-(butanone oxime)Silane, Methyl Oximino Silane, Methyl tris-(methyl ethyl ketoximo)Silane, Phenyl tris-(butanone oxime)Silane, Tetraethoxysilane, Tetra(methyl ethyl ketoximo)Silane, Tetramethoxysilane, Vinyltriethoxysilane, Vinyltrimethoxysilne, Vinyl tris-(butanone oxime)Silane, Vinyl Oximino Silane, or Vinyl tris-(methyl ethyl ketoximo)Silane.

* * * * *